United States Patent [19]

Steigelmann

[11] 4,014,665

[45] Mar. 29, 1977

[54] MEMBRANE PROCESS AND PRODUCT
[75] Inventor: Edward F. Steigelmann, Naperville, Ill.
[73] Assignee: Standard Oil Company (Indiana), Chicago, Ill.
[22] Filed: Oct. 7, 1974
[21] Appl. No.: 512,972
[52] U.S. Cl. .................................. 55/16; 210/23 H; 210/500 M; 210/501; 260/677 A; 260/679 A
[51] Int. Cl.$^2$ ........................................ C07C 11/12
[58] Field of Search ................ 55/16, 158; 210/22, 210/321, 23, 500 M, 63, 501; 117/138.8 H; 260/677 A, 679 A

[56] References Cited

UNITED STATES PATENTS

| | | | |
|---|---|---|---|
| 2,008,131 | 7/1935 | Dieck et al. | 210/501 X |
| 3,088,791 | 5/1963 | Cline et al. | 117/138.8 H X |
| 3,246,767 | 4/1966 | Pall et al. | 210/505 |
| 3,276,996 | 10/1966 | Lazare | 210/22 |
| 3,327,859 | 6/1967 | Pall | 210/266 |
| 3,758,603 | 9/1973 | Steigelmann et al. | 55/16 X |
| 3,843,516 | 10/1974 | Yamada et al. | 210/63 X |

Primary Examiner—Frank A. Spear, Jr.
Attorney, Agent, or Firm—Morton, Bernard, Brown, Roberts & Sutherland

[57] ABSTRACT

There is described an improved membrane-liquid barrier system of the type containing complex-forming, silver-containing ion component in an aqueous solution, and an improved process in which the membrane-liquid barrier combination can be employed to separate olefinically-unsaturated hydrocarbons. The membrane is in contact with an aqueous solution having dissolved therein complex-forming silver-containing ions, and further includes small but effective amounts of hydrogen peroxide to retard reduction of the ionic silver to elemental silver.

16 Claims, No Drawings

MEMBRANE PROCESS AND PRODUCT

This invention relates to separation systems in which are employed a semi-permeable membrane in contact with an aqueous solution having dissolved therein complex-forming, silver-containing ions, and to processes of separating materials from fluid mixtures by the use of such membrane-liquid barrier combinations. The semi-permeable film membranes of this invention are in contact with an aqueous solution of the complex-forming, silver-containing ions, and the solution further contains hydrogen peroxide in an amount sufficient to retard reduction of the silver-containing ions to elemental silver and to thereby improve performance of the separation process. The separations of this invention are thus performed by the combined use of liquid barrier permeation and metal complexing techniques wherein the liquid barrier having complex-forming, silver-containing ions in aqueous solution is contiguous to, or, preferably, at least partly contained in the semi-permeable membrane. The liquid barrier-membrane systems are especially useful for separating olefinically-unsaturated hydrocarbons for mixtures containing the hydrocarbons to be separated along with other material.

There is considerable commercial interest in separating olefinically-unsaturated hydrocarbons from mixtures containing them. These olefinically-unsaturated hydrocarbons are reactive materials that serve in various roles, generally in chemical syntheses. A number of the olefinically-unsaturated hydrocarbons are employed as monomers in the formation of polymers and, in this regard, olefins such as ethylene, propylene, butadiene and isoprene are well known. These olefins are also used to form relatively low molecular weight products.

The olefinically-unsaturated hydrocarbons are most often made available on a commercial basis in admixture with other chemical compounds, frequently other hydrocarbons. These unsaturated hydrocarbon-containing streams are usually by-products of chemical syntheses or separation processes. When the hydrocarbon streams are liquid under normal conditions or can readily be made so, ordinary distillation techniques can be used to separate the hydrocarbon components providing they have sufficiently different boiling points for the process to be economically feasible. Especially when the hydrocarbon mixtures contain materials having close boiling points, which is frequently the case with hydrocarbons of the same number of carbon atoms or having a difference of only one carbon atoms, distillation may not be an attractive separation procedure. In such situations, more expensive processes are often used and involve operations such as solvent extraction or extractive distillation which entail considerable expense, if indeed they are technically feasible in a given situation.

When the mixture containing the olefinically-unsaturated hydrocarbon is essentially in a gaseous state at normal at ambient conditions of temperature and pressure, separation of the desired component from the mixture may be even more troublesome. In these situations, cryogenic processes may be used, but they are expensive. The components of these normally gaseous mixtures may not even have particularly close boiling points, but, nevertheless, the mixtures must be cooled in order to separate one or more of its components. In spite of the considerable cost of cryogenic operations, the procedure has been employed commercially for the separation of ethylene from other gaseous materials such as ethane and methane.

Systems are now known which are directed to methods for separating various materials from mixtures containing them, and involve the combined use of liquid barrier permeation and metal complexing techniques which can exhibit high selectivity factors. In the processes, the liquid barrier is an aqueous solution having dissolved therein metal-containing ions which will complex with the component to be separated, and the liquid barrier is employed in contact with a semi-permeable membrane which is essentially impremeable to the passage of liquid. Preferably the liquid barrier containing the complex-forming, metal-containing ions is at least partially contained in the semi-permeable film membrane and this occurs when the liquid barrier is in contact with a hydrophilic membrane. When operating in this manner, there is no need to maintain contact of the film with a separate or contiguous aqueous liquid phase during the process, although such a separate liquid phase may be present. These membranes employed are fairly stable, have satisfactory permeability and exhibit good selectivity for separating various complex-forming materials, e.g., olefinically-unsaturated hydrocarbons.

In systems for conducting these separations essentially the entire aqueous liquid can be disposed as a distinct liquid phase contiguous to and on the feed side of the semi-permeable membrane film, wherein the mixture to be separated is introduced into the liquid phase. The aqueous liquid phase has also been held in contact with a semi-permeable membrane film by absorbing the liquid in a porous inert solid such as filter paper, and holding the wet paper next to the semi-permeable membrane in, for instance, a sandwich-type cell construction. While these separate liquid phase and sandwich-type membranes may be successfully employed in separation systems, the liquid barrier-containing membranes are preferred because they afford greater shape and manufacturing flexibility and offer higher separation rates for a given investment in equipment. Also, sandwich membranes cannot be readily fabricated into hollow fiber form which offers high surface area for contact between the membrane and the material to be separated.

In the separation system, however, it has been found that the complex-forming metal ion component having silver-containing ions therein may be rendered less effective over prolonged use due to the reduction of the silver-containing ions to elemental silver by light or a variety of mild reducing agents that may be encountered in the system. The selectivity and separation ability of the membrane decreases as the complexing silver-containing ions are reduced to their elemental state. In the present invention, however, these problems are alleviated by including hydrogen peroxide in the complex-forming, silver-containing ion solution. The novel membrane-liquid barrier combinations of this invention employing the complex-forming, silver-containing ion solution with the hydrogen peroxide are advantageously used in separation processes in which the hydrogen peroxide retards reduction of the silver-containing ions, enhances membrane selectivity, and results in superior processes which may be carried out at high feed capacities over prolonged periods of time. In addition, the separation processes of this invention are less costly than those operating without hydrogen peroxide in the liquid barrier, since shut-downs for membrane reactivation are less frequent and complex-forming metal component material costs are correspondingly decreased.

In the olefin separation method of the present invention the hydrogen peroxide is in the liquid barrier in an amount sufficient to significantly retard reduction of the complex-forming, silver-containing ions to their elemental state, and this amount usually serves to enhance prolonged separation selectivity in the process. Generally, the amount of hydrogen peroxide is a minor amount, say at least about 0.01 weight percent and often up to about 10 weight percent, preferably about 0.1 weight percent to about 3 weight percent, based on the weight of the barrier solution.

The amount of water in the liquid barrier employed in this invention may be a minor portion of the liquid phase, but preferably is a major portion or even essentially all of the liquid, on a complex-forming, silver-containing ion component-free basis. Thus, small or minor amounts of water, say as little as about 5 weight percent, on a complex-forming, component-free basis in the liquid phase may serve to provide significant transport of the material to be separated across the liquid barrier. Generally, there may be from about 10 weight percent up to about 90 weight percent water, preferably about 20 weight percent up to about 60 weight percent, based on the weight of the barrier solution. Any other liquid present in the barrier is preferably water-miscible and should be chosen as not to have a substantial deleterious effect on the separation to be accomplished. The liquid barrier may also contain a hygroscopic agent, e.g., in a minor amount, to improve the wetting or hydrophilic properties of the liquid and provide better contact with the feed gas. Further, additional water-soluble salts, preferably $NO_3^-$ or $BF_4^-$-containing salts, e.g., their sodium salts, may be included to increase the ionic strength of the solution.

When hydrophilic semi-permeable membranes are used in this invention they can be provided with the complex-forming, silver-containing ions by impregnation of the film with an aqueous solution containing the ions, and the hydrogen peroxide may be included therewith or may be added by impregnation or supplied in both of these ways. By using a small differential pressure across the film, impregnation may be enhanced, but one must be careful not to rupture or otherwise deleteriously affect the physical integrity of the film. Alternatively, the complex-forming component can be placed within the membrane of this invention by using a liquid solution containing both the film-forming material and the complex-forming, silver-containing ion component dissolved in the solution. Thus, the solution may contain liquid solvent which may include water, liquid organic or inorganic solvent or combinations of such materials. The solvent can be formulated so that the film-forming material and complex-forming component will be soluble in the liquid phase to provide a relatively homogeneous film-forming composite. This solution is then used to make the essentially solid, semi-permeable membrane by an appropriate film-forming technique such as casting.

In those instances in which film-forming constituents may be detrimental to the hydrogen peroxide or in which the film-forming constituents may be detrimentally affected by the hydrogen peroxide, the hydrogen peroxide should be added to the film membrane after it has been formed. This may apply, for example, in some instances where a solvent other than water is employed for the film-forming constituents. Membranes containing the complex-forming metal component may be stored in a dry state and subsequently wetted before use. In this case it may be desirable to include the hydrogen peroxide in the wetting solution in an effective amount rather than in the original film-forming solution. Additionally, the hydrogen peroxide or a solution containing the hydrogen peroxide, and/or the complex-forming metal component may be fed to the liquid barrier either intermittently or continuously from either the inlet or the outlet side of the membrane, or both, during use or between periods of use. Advantageously, when a solution containing both the hydrogen peroxide and the complex-forming component, e.g. water containing, for example, from about 0.1 to 3% hydrogen peroxide and about 2 to 6 molar $AgNO_3$, is fed to the membrane system, metallic silver, which might be undesirably present in the membrane, may be removed. Thus, such undesirable silver deposits are dissolved or inhibited by treating the membrane in this manner, and silver metal which has formed can thereby be removed.

In the present invention, the essential metal which serves in the form of metal-containing cations to separate an olefinically-unsaturated component from a mixture through the formation of metal complexes of desired properties, is, as mentioned, silver, although other complex-forming metals may be included with the silver. These include metals of the Periodic Chart of Elements having atomic numbers above 20.

The silver ions are provided in the film or in aqueous liquid barrier of the separation system in a form which is soluble in this liquid. Thus, the various water-soluble salts can be used such as the nitrates, fluorides, fluoborates, fluosilicates, acetates, carbonyl halides or other salts which can serve to form the desired water-soluble complexes when the film is in contact with water. The metal salts should not react with any components of the chemical feedstock used in the separation procedure to form an insoluble material which could block the film membrane or otherwise prevent the separation of a component from the feedstock. Also, in a given system, the salt is selected so that the complex will readily form, and yet be sufficiently unstable, so that the complex will decompose and the disassociated material leave the liquid barrier, thereby providing a greater concentration of the material to be separated from the exit side of the membrane than is in the feed. Particularly advantageous silver salts which may be used with hydrogen peroxide in the separation process of this invention are silver nitrate and silver tetrafluoroborate. The concentration of the silver-containing ions in the film or liquid barrier may be rather low and still be sufficient to provide an adequate complexing rate so that excessive amounts of the semi-permeable membrane surface will not be needed to perform the desired separation. Conveniently, the concentration of the complex-forming, silver-containing ions in the aqueous solution forming the liquid barrier is at least about 0.1 molar, and is preferably about 0.5 to 12 molar. Advantageously, the solution its less than saturated with respect to the complex-forming, silver-containing ions to insure that essentially all of the silver stays in solution, thereby avoiding any tendency to plug the film membrane and destroy its permeability characteristics. In the system of the present invention, in which the liquid barrier is in the semi-permeable membrane, the amount of complex-forming component in the semi-permeable membrane may vary considerably, but is sufficient to accomplish the desired separation. Often, this is a minor amount, say, about 1 to 50 weight percent, of the weight of the membrane on a non-aqueous basis, preferably about 5 to 25 weight percent.

The membrane containing the complex-forming component may be handled and transported in an essentially non-aqueous form with or without the hydrogen peroxide, but perferably without the hydrogen peroxide if in otherwise dry form, or with some water therein, for instance, an insufficient amount of water to be effective in the separation. In such case, water with the hydrogen peroxide where necessary could be added to the membrane to give a film bearing sufficient water to be useful in performing the separation process of the invention. During use of the membrane, the amount of water present may be less than that which gives a substantial distinct or separate aqueous phase on the feed inlet side of the membrane. The film membrane can be wetted initially, and if it has a tendency to dry during use, additional water with or without hydrogen peroxide can be placed in the film while it is used on-stream in the separation process of this invention, for instance, by inclusion of moisture in the gaseous feed charged to the system. Alternatively, but less advantageously, the operation can be stopped for addition of water to the film. The water could be added at intervals by stopping the feeding of the gaseous mixture to the system, and charging water to the membrane of such times. In any event, care should be taken to insure that the film membrane during use is not so dry that it will exhibit non-selective permeability to the material to be separated from the feed, and will thereby not serve to separate a product having an increased concentration of the desired ingredient.

The membrane films employed in the process of this invention may be the types which have been used in conjunction with complex-forming metal solutions, see, for instance, U.S. Pat. Nos. 3,758,603 and 3,758,605, incorporated herein by reference, but preferably are of the essentially water-insoluble, hydrophilic, semi-permeable type. A film membrane may be considered hydrophilic if it absorbs at least about 5 weight percent of water when immersed in distilled water for one day at room temperature and pressure. In the absence of the liquid containing the complex-forming ions, the film is generally not adequately selective with respect to the passage of or permeation by the material to be separated to perform the desired separation at the desired rate. Often, the film is permeable to essentially all of the components in the gaseous feedstock used in this invention. However, by having the film in contact with sufficient aqueous liquid to form a barrier, the simple diffusion of gas through the film is reduced or prevented, and the components of the feed stream must, therefore, traverse the film primarily be becoming part of, and then being separated from, the aqueous liquid phase in contact with the film. Thus, in the absence of the complexing silver-containing ion component in the aqueous medium, there could be a slight separation effected by the use of water as the liquid medium since the individual components in the gas may exhibit differing solubilities in water. In the method of the present invention, however, the selectivity of the separation is greatly increased due to the presence of the complex-forming, silver-containing ions in the aqueous barrier medium. Also, during use in the process of this invention, there is a sufficient amount of the aqueous medium present so that adequate silver-containing ions are in solution, or at least react as if they are, to perform the desired separation.

Among the film-forming materials which may be employed in the present invention are the hydrophilic types including those which have heretofore been used for separation or purification of various chemical materials. Among these are the film-forming materials disclosed in U.S. Pat. Nos. 3,228,877 and 3,566,580, incorporated herein by reference. Advantageously, the materials which can be employed to provide the semi-permeable film membranes used in the present invention are those having a polyamide as an essential constituent. The polyamide film-forming materials are generally known and have also been designated as nylons. These polymers are characterized by having amide groups serving as recurring linkages between carbon chains in the product structure, and the polymers may be made by several procedures. Commonly, the polyamides are formed by reacting a polyamine and a dicarboxylic acid or its derivative such as an ester, especially a lower alkyl ester having, for instance, about 1 to 4 carbon atoms in each ester group. Other reactions which may be employed to form the polyamides include the self-condensation of monoamino, monocarboxylic acids and the reactions of cyclic lactams. In any event, the polyamide products contain recurring amide groups as an integral part of the principle polymer chain. The polyamides are described, for instance, in the Kirk-Othmer, *Encyclopedia of Chemical Technology*, Second Edition, Volume 16 beginning at page 1, Interscience Publishers, New York, 1968. Among the typical structural formulas of the linear polyamides are $H_2NRNH(COR'CONHRNH)_nCOR'COCH$ and $H_2NRCO(NHRCO)_nNHRCOOH$, where R and R' represent primarily carbon-to-carbon chains between functional groups in the reactants, and $n$ represents the degree of polymerization or the number of recurring groups in the polymer chain. The polyamides which can be used in this invention are generally solid at room temperature, and have a molecular weight which makes them suitable for forming the desired film membranes. Polyamides of this type are described in, for instance, U.S. Pat. No. 3,355,409.

The carboxylic acids which may be used in forming the polyamides have an acyloxy group ($-R-COO-$) in their structure and the R member of this group is composed essentially of carbon and hydrogen and often contains about 6 to 12 carbon atoms. Such groups may be aliphatic, including cycloaliphatic, aromatic, or a mixed structure of such types, but the groups are preferably aliphatic and saturated with respect to carbon-to-carbon linkages. These R groups may preferably have straight chain carbon-to-carbon or normal structures. Among the useful dicarboxylic acid reactants are adipic acid, sebacic acid, azelaic acid, isophthalic acid, terephthalic acid, and the methyl esters of these acids.

The polyamines employed in making the polyamide film-forming membranes generally have at least two non-tertiary, amino nitrogen atoms. These nitrogen atoms may be primary or secondary in configuration, although amines having at least two primary nitrogen atoms are preferred. The polyamines may also have both primary and secondary nitrogen atoms and the polyamines may contain tertiary nitrogen atoms. The preferred polyamine reactants have aliphatic, including cycloaliphatic, structures, and often have from 2 to about 12 carbon atoms. Also, the preferred polyamines are saturated and have straight-chain structures, although branched-chain polyamines can be used. Among the useful polyamines are ethylene diamine, pentamethylene diamine, hexamethylene diamine, diethylene triamine, decamethylene diamine and their N-alkyl substituted derivatives, for instance, the lower alkyl derivatives which may have, for instance, 1 to 4 carbon atoms in each alkyl substituent.

Film-forming polymers which can be employed with special advantage in this invention are those in which the film-forming polyamide is an N-alkoxyalkyl-substituted polyamide. Materials of this type are well known, as shown, for instance, by U.S. Pat. Nos. 2,430,910, and 2,430,923, which disclose N-alkoxymethyl polyamides made by the reaction of a polyamide polymer, formaldehyde and alcohol. Generally, at least about 5% of the amide groups of the polymer are substituted with alkoxyalkyl groups and such substitution may be up to about 60% or more. Preferably, this substitution is about 10 to 5% with the product being soluble in hot ethanol.

The alcohols employed in making the N-alkoxyalkyl polyamides are generally monohydric and may have, for instance, from 1 to about 8 or more carbon atoms. The lower alkanols are preferred reactants, especially the lower alkanols having 1 to 4 carbon atoms. Among the useful alcohols are methanol, propanols, butanols, oleyl alcohol, benzyl alcohol, lauryl alcohol and alcohol ethers, for instance, the alkyl ethers of ethylene glycol.

The N-alkyloxyalkyl polyamides which can be employed as film-forming materials in the present invention to provide the desired semi-permeable membrane may be reacted with cross-linking agents. Such agents may be, for example, polycarboxylic acids, especially the dicarboxylic acids which may have, for instance, from 2 to about 12 carbon atoms. Useful acids include oxalic acid, citric acid, maleic acid, and the like.

Film-forming membranes which can advantageously be employed in the present invention can be made by intimately combining, by either physical means or through chemical reaction, the N-alkoxyalkyl polyamide and a hygroscopic polymer material, e.g., the water-soluble polyvinyl alcohols. The polyamides and hygroscopic polymer may be used as a physical admixture or in various reacted forms, for instance, as cross-linked polymers or block or graft copolymers. The hygroscopic polymer is generally employed in an amount sufficient to enhance the hydrophilic properties of the polyamide and may be up to about 75 weight % or somewhat more of the membrane composition based on the total polyamide and hygroscopic polymer, and the latter is often at least about 5 or 15% and the amount is sufficient to impart a significant property to the film-forming combination. Preferably, each of the hygroscopic polymer and the polyamide are about 25 to 75% of their combination or total amount, or the hydroscopic polymer may be about 35 to 55% and the polyamide about 45 to 65% of their combination.

The polyvinyl alcohols which can be employed in the membranes used in the present invention are essentially water-soluble materials, at least in hot water, and many of these are commercially available. The molecular weights of these polymers are often at least about 1000, and are commonly in the range of about 10,000 to 300,000 or more. Suitable polyvinyl alcohols are described in, for example, "Water-Soluble Resins", Second Edition, Edited by Robert L. Davidson and Marshall Sittig, pages 109 to 115, Reinhold Book Corporation, New York, N.Y. The polyvinyl alcohol may be cross-linked, especially after the membrane is formed from the polymeric materials. The presence of the cross-linked polyvinyl alcohol may increase the strength of the membranes and increase their resistance to loss of polyvinyl alcohol by leaching during use. The polyvinyl alcohol may be cross-linked, for example, by reaction with formaldehyde, e.g., by immersing the fibers in an aqueous bath containing 40% $(NH_4)_2SO_4$ and 10% HCHO and 7½% $H_2SO_4$, at 50° C. for 1 to 3 hours.

Cross-linking of the N-alkyloxyalkyl polyamides can be accomplished by contact of the membranes with an organic or inorganic acidic catalyst such as a sulfonic acid of an aromatic hydrocarbon, mild nitric acid and the like. Such catalysts may, for instance, be naphthalene or toluene sulfonic acids, and cross-linking can be accomplished at elevated temperatures. During contact of the membrane with the acid catalyst as an aqueous solution, it is preferred that a water-soluble alkali metal salt be dissolved in the solution to maintain the integrity of the polyvinyl alcohol by reducing its tendency to dissolve in the aqueous catalyst solution. Cross-linking or other modification of the polymer composition may be effected before, during or after it is formed into the shape in which it is going to be used, but if this occurs before shaping, the modification should not be so extensive that the desired shaping may not be accomplished.

The film membranes which can be employed in this invention are preferably self-supporting and have sufficient strength not to require any additional supporting material on either of its sides during use. With some films, however, it may be necessary, advantageous or convenient to provide adaquate support such as additional film or sheet-like materials on one or both sides of the film membrane. These supporting structures are frequently very thin materials and may be permeable to both liquids and gases and not serve a separating function with respect to any component of the feed stream. Alternatively, the supporting film may be permeable to gases, but not to liquids.

The film membranes may be in the form of flat disc-like films, for example, or may be extruded membranes in the form of thin hollow fibers. In flat form the film membranes may have a thickness of up to about 30 mils or more. Preferably the thickness is up to about 10 or 15 mils. The films are sufficiently thick to avoid rupture during use and generally have a thickness of at least about 0.05 mil. In one preferred embodiment the membranes are formed by extrusion into thin walled fibers, the overall diameter of which may be up to about 75 or more mils, preferably about 0.5 to 30 mils, with walls having a thickness of about 30 mils or more, preferably about 0.2 to about 15 mils, and often at least about 0.05 mil.

The process of this invention can be employed to separate various olefinically-unsaturated materials from other ingredients of a fluid feed mixture providing at least one of the materials in the mixture exhibits a complexing rate or transfer rate across the liquid barrier in the film that is greater than at least one other dissimilar or different component of the feedstock.

Although the separated materials thus provided may be quite pure materials, for instance, of greater than 99% purity, the separation procedure may be used merely to provide a significant increase in the concentration of a given material in a mixture with other components of the feedstock.

Quite advantageously, the process of this invention can be used to separate olefinically-unsaturated hydrocarbons, e.g. monoolefins or diolefins, from other hydrocarbons which may be aliphatically saturated or from non-hydrocarbon materials, including fixed gases such as hydrogen. The feed mixture may thus contain one or more paraffins, including cycloparaffins, mono- or polyolefins, which may be cyclic or acyclic, and the mixture may include aromatics having such aliphatic configurations in a portion of their structure. Often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, and the like. Since silver may form an explosive acetylide, the presence of significant amounts of acetylenes in the feed mixture should be avoided. The process can thus be used to separate paraffins from monoolefins or diolefins. The feed need only contain a small amount of olefinically-unsaturated hydrocarbon, as long as the amount is sufficient so that the unsaturated material to be separated selectively reacts with the metal complex ions to a significant extent, and thus at least one other component of the feed is less reactive or non-reactive with the complex-forming metal ions.

The olefinically-unsaturated materials of most interest with regard to separation have 2 to about 8 carbon atoms, preferably 2 to 4 carbon atoms. The separation of olefinically-unsaturated materials from admixtures containing other gaseous materials, such as the separation of ethylene or propylene from admixtures with other normally gaseous materials, e.g., one or more of ethane, propane, and methane and hydrogen, is of particular importance. Frequently such feed mixtures for the process contain about 1 to 50 weight percent ethylene, about 0 to 50 weight percent ethane and about 0 to 50 weight percent methane.

The partial pressure of the olefinically-unsaturated component of the feed to be separated, is at the input side of the liquid barrier used in the separation, greater than the partial pressure of this unsaturated hydrocarbon on the discharge or exit side of the liquid barrier-semi-permeable membrane composite. This pressure drop of the unsaturated hydrocarbon to be separated may often be at least about 0.5 pound per square inch, and is preferably at least about 20 psi, although the pressure drop should not be so great that the liquid barrier or semi-permeable membrane is ruptured or otherwise deleteriously affected to a significant extent. Conveniently, the total pressure of the feed is up to about 1000 pounds per square inch. The discharge partial pressure of the unsaturated hydrocarbon can preferably be controlled by subjecting the exit side of the liquid barrier to the action of a sweep gas that may be essentially inert to forming a complex with the metal ions in solution in the liquid barrier. The sweep gas picks up the discharged olefinically-unsaturated components, and the sweep gas may be selected so that it can be readily separated from the olefinically-unsaturated hydrocarbon material if that be necessary for the subsequent use of the unsaturated hydrocarbon. Unless a reaction with the separated hydrocarbon is desired, the sweep gas should be relatively inert therewith and may be, for instance, butane, carbon dioxide or the like. Alternatively, the separated material may be removed from the exit side through the effect of a vacuum on the exit side of the barrier.

The temperature across the liquid barrier-semi-permeable film composite employed in the separation procedure can be essentially constant or it may vary, and decomposition of the metal-unsaturated hydrocarbon complex can be affected primarily by the drop in partial pressure of the olefinically-unsaturated hydrocarbon on the exit side of the liquid barrier compared with the partial pressure on the feed side. Conveniently, the temperature of the liquid barrier may be essentially ambient, especially in the case of feedstocks that the gaseous at this temperature and the pressure employed on the feed side of the liquid barrier. The temperature of the liquid barrier may, however, be reduced or elevated from ambient temperature. Often the temperature may be up to about 100° C., and elevated temperatures may even be desired to put the feedstock in the gaseous or vapor phase. Neither the temperature nor the pressure used should, however, be such as to destroy the difference in transport rate across the liquid barrier-semi-permeable film composite, of the olefinically-unsaturated hydrocarbons whose separation is sought, compared with that of the other components of the feed. The conditions should also not be such that physical disruption of the liquid barrier or semi-permeable membrane, or any other significant malfunction results.

The methods and products of this invention and their value are shown further by the following examples. Unless otherwise indicated, the percentages given are on a weight basis.

EXAMPLE 1

A blend of 128 gms. of formaldehyde-alcohol modified 6:6 nylon (BCI-819, Belding Chemical Industries), 72 gms. of polyvinyl alcohol (determined by gel permeation to have a number average molecular weight of about 12,360 and 0 to 0.5% acetate), 200 ml. of dimethyl sulfoxide (DMSO) and 20 ml. of water was made as an extrusion mix by first mixing the polymers and then adding the DMSO and water. The resulting mix was then heated to 260° F. under agitation for about an hour before extrusion. The polymer mixture was then extruded through an annular die and air was passed through a hypodermic needle positioned in the center of the die to insure formation of hollow fibers. Hollow fibers were produced which had a 0.010 inch diameter and a 0.018 inch outer diameter.

Four of the hollow fibers each having a total length of about 19 inches were potted into a fiber bundle unit (Unit 1) using Dow Sylgard 184 resin and the resulting potted fiber bundle was soaked in a 2N $AgNO_3$ solution positioned on the outside of the fibers while the fiber bundle was in place in a cell designed for use in the separation process. A 20 p.s.i.g. pressure differential was applied between the outside and the inside of the fibers for a period of 1 hour to drive the solution into the fibers. The bundle was positioned in the cell so that about 12 inches of the length of each fiber would be exposed to the feed mixture used in the separation process.

EXAMPLE II

Four more fibers extruded as described in Example 1, each having a total length of about 19 inches, were potted into a fiber bundle unit (Unit 2) using Dow Sylgard 184 resin, and the resulting potted fiber bundle was soaked in a 2N AgNO$_3$ solution which contained about 0.5% H$_2$O$_2$. During soaking the solution was on the outside of the fibers and a 20 p.s.i.g. pressure differential from the outside to the inside of the fibers, was applied for one hour to drive the solution into the fiber and to produce the novel fiber membranes of this invention. As the bundle was positioned in the separation cell the length of each fiber that would be exposed to the feed mixture used in the separation process, was again about 12 inches.

To test the fiber bundle units produced according to Examples 1 and 2 and to illustrate the advantages of the present invention in which hydrogen peroxide is included in the complexing solution as in Example 2, each of the units was assembled into a hollow fiber test cell in which the fibers had a total effective membrane area of 13.2 cm$^2$. Each unit identically had a methane-ethane-ethylene mixture passed through the inside of the fibers at 20 p.s.i.g. and at a total flow rate of 10 ml./min. (STP). The feed mixture contained 20.70% CH$_4$, 35.61% C$_2$H$_4$, and 43.69% C$_2$H$_6$. A nitrogen purge supersaturated with water flowed in direction countercurrent to the feed at atmospheric pressure and at a rate of 10 ml./min. over the outside of the fibers. The excess water in the purge kept the fibers wet. The purge picked up the products permeating the fiber walls and an analysis of the purged products was made by gas-chromatography. The results are shown in TABLE 1., below:

TABLE 1

Effect of H$_2$O$_2$ On Membrane Performance For Purifying Ethylene, Product Analysis

| Unit | No. of Days on Stream | % CH$_4$ | % C$_2$H$_4$ | % C$_2$H$_6$ | S* | P ml/cm$^2$ min |
|---|---|---|---|---|---|---|
| 1. (with AgNO$_3$) | 1 | .38 | 98.89 | .73 | 162 | .0049 |
|  | 2 | .91 | 97.27 | 1.82 | 64 | .0069 |
|  | 3 | .96 | 97.20 | 1.83 | 63 | .0063 |
|  | 6 | 1.40 | 96.20 | 2.41 | 45 | .0050 |
|  | 7 | 3.20 | 90.74 | 6.06 | 18 | .0022 |
|  | 8 | 2.03 | 94.58 | 3.39 | 31 | .0034 |
|  | 9 | 2.29 | 94.07 | 3.64 | 29 | .0033 |
|  | 10 | 1.44 | 95.98 | 2.58 | 43 | .0039 |
| 2. (with AgNO$_3$ and H$_2$O$_2$) | 1 | .26 | 99.30 | .44 | 259 | .0090 |
|  | 2 | .25 | 99.30 | .45 | 257 | .0257 |
|  | 3 | .34 | 99.11 | .55 | 201 | .0217 |
|  | 6 | .72 | 97.90 | 1.39 | 84 | .0114 |
|  | 7 | .49 | 98.68 | .82 | 136 | .0173 |
|  | 8 | .80 | 97.85 | 1.36 | 82 | .0106 |
|  | 9 | .63 | 98.33 | 1.03 | 106 | .0137 |
|  | 10 | .75 | 97.96 | 1.28 | 87 | .0104 |

$$*S = \text{Selectivity factor} = \frac{[C_2H_4]\text{product}}{[C_2H_6+CH_4]\text{product}} \times \frac{[C_2H_6+CH_4]\text{feed}}{[C_2H_4]\text{feed}}$$

As shown by the table, Unit 2 using membrane having the solution containing hydrogen peroxide had a higher permeability, P, and a better selectivity, S, than did Unit 1 in which the solution did not contain hydrogen peroxide. Unit 2 had about a several-fold advantage over Unit 1 over the 10 test days in both permeability and selectivity. Both units exhibited a decrease in performance with time which could be counteracted by adjusting the amounts of water included in the entering purge gas.

In the above test, Unit 1 fibers had turned black during operation while the fibers of Unit 2 remain white. The black color evidences the reduction of ionic silver to silver metal and the avoidance of black discoloration in Unit 2 evidences the prevention of metal reduction by the hydrogen peroxide.

EXAMPLE III–V

As examples of different modes of operation of this invention, the following Examples III–V were performed:

Fibers were prepared from a polymer mixture containing 180 gms BCI-819 nylon (Belding Chemical Industries), 120 gms polyvinyl alcohol (DuPont's Elvanol 71—30), 270 ml dimethyl sulfoxide, and 30 ml water. The mixture was extruded through an annular die (O.D.=0.030 inch and I.D.=0.014inch). The polymer was passed through the annulus of the die at the rate of 12 ml/min while air was pumped through the center of the die at the rate 0.382 ml/min. In this manner a fiber was produced which had an O.D. of 0.0237 inch and an I.D. of 0.0072 inch. The fiber exiting the extruder was quenched in an acetone bath for at least 30 min, and then air dried. The nylon polymer in cross-linked by immersing the fibers in a bath containing 3% p-toluene sulfonic acid and 5% Na$_2$SO$_4$ at 50° C for 1 hour. Following this, the fibers were washed three times in distilled water to remove any of the remaining cross-linking bath salts.

Next, the fibers were oriented by passing them through a 4-foot long tube furnace at 80° C and at the rate of 3 feet/min. While they were passing through the furnace, they were stretched with a 200 gm weight. After this orientation they were annealed at 170° C for 10 min while under no stress. The final fibers had an O.D. of 0.0215 inch and an I.D. of 0.0055 inch.

Six 19 inch sections of this fiber were potted into a unit using Sylgard (Dow) 184 encapsulating agent. After the potting was completed 12 inches of active length for each fiber and a total fiber area for the unit of 18.4 cm$^2$ were obtaind between potting joints.

This fiber bundle was tested in a separation unit under three modes of operation, and in all the feed was on the outside of the fibers at a pressure 100 p.s.i.g. and at a flow of 2 ml/min and with a helium purge stream on the inside of the fibers at about atmospheric pressure and at a flow of 2 ml/min. For Example III, the shell side of the bundle was filled with a 6 N AgNO$_3$ + 0.3% H$_2$O$_2$ aqueous solution, and a 0.3% H$_2$O$_2$ aqueous solution was trickled through the inside length of the fibers at the rate of 0.0019 ml/min. For Example IV, the shell side was filled with a 6 N AgNO$_3$ + 0.3% H$_2$O$_2$ aqueous solution and a 4 N AgNO$_3$ + 0.3% H$_2$O$_2$ solution was trickled through the inside length of the fibers at the rate of 0.0016 ml/min. For Example V, the shell side was free of solution with a 4 N AgNO$_3$ + 0.3% H$_2$O$_2$ solution was trickled through the inside length of the fibers at the rate of 0.0016 ml/min.

The results of this test and the number of days for each mode are given in accompanying Table 2. The results show that operations for all three modes were comparable.

TABLE 2

Comparison of General Methods for Operating Membrane Unit
(Feed Pressure = 100 psig; Feed Rate = 2 ml/min;
Purge Rate = 2 ml/min)

| Unit | No. of Days on Stream | Wt% $CH_4$ | Product Wt% $C_2H_4$ | Wt% $C_2H_6$ | P ml/cm² min |
|---|---|---|---|---|---|
| (Feed Example III | — | 20.59 | 40.13 | 39.28) | — |
| Example III (6 N $AgNO_3$ + 0.3% $H_2O_2$ outside and 0.3% $H_2O_2$ inside) | 8 | 0.32 | 99.26 | 0.42 | .00208 |
| Example IV (6 N $AgNO_3$ + 0.3% $H_2O_2$ outside and 4 N $AgNO_3$ + 0.3% $H_2O_2$ inside) | 7 | 0.40 | 98.99 | 0.61 | .00174 |
| Example V (nothing outside and 4 N $AgNO_3$ + 0.3% $H_2O_2$ inside) | 9 | 0.34 | 99.17 | 0.49 | .00184 |

It is claimed:

1. A membrane-liquid barrier system, comprising an essentially solid, water-insoluble, semi-permeable membrane film and an aqueous liquid barrier in contact with said film, said liquid barrier having dissolved therein a complex-forming, silver-containing ion component having silver essentially in solution, and hydrogen peroxide in an amount sufficient to retard reduction of the ions in said ion component.

2. The system of claim 1 wherein said semi-permeable membrane film is hydrophilic.

3. The system of claim 1 wherein said liquid barrier contains from about 0.01% to avbout 10% by weight of hydrogen peroxide based on the weight of aqueous liquid barrier.

4. The system of claim 1 wherein said complex-forming, silver-containing ion component includes silver nitrate.

5. The system of claim 2 wherein said membrane film comprises nylon.

6. The system of claim 5 wherein said membrane film comprises nylon and polyvinyl alcohol.

7. The system of claim 6 wherein said aqueous liquid barrier contains from about 0.1% to about 3% by weight of hydrogen peroxide based on the weight of the aqueous liquid barrier, and the concentration of the silver-containing ions in the aqueous liquid barrier is at least about 0.1 molar.

8. The system of claim 5 wherein said complex-forming silver-containing ion component includes silver nitrate.

9. In a method for separating an olefinically-unsaturated material from a fluid mixture containing said material and at least one other component which comprises contacting said mixture with a first side of an essentially solid, water-insoluble, semi-permeable membrane in contact with an aqueous liquid barrier having dissolved therein a complex-forming, silver-containing ion component which combines with said material to form a water-soluble complex, the partial pressure of said material on a second side of said semi-permeable membrane being sufficiently less than the partial pressure of said material in said mixture to provide separated material on said second side of said semi-permeable membrane, and providing dissociated separated material from said water-soluble complex on said second side of said semi-permeable membrane and removing said separated dissociated material from the vicinity of said second side of said semi-permeable membrane, the improvement which comprises providing hydrogen peroxide in said aqueous liquid barrier in an amount sufficient to retard reduction of the ions in said ion component.

10. In a method for separating olefinically-unsaturated hydrocarbon of 2 to 4 carbon atoms which comprises contacting a vaporous mixture containing said olefinically-unsaturated hydrocarbon with a first side of an essentially solid, water-insoluble, semi-permeable membrane in contact with an aqueous liquid barrier said semi-permeable membrane being permeable to said vaporous mixture in the absence of said aqueous liquid, said liquid barrier having dissolved therein a complex-forming silver-containing ion component which combines with said unsaturated hydrocarbon to form a water-soluble complex, the partial pressure of said unsaturated hydrocarbon on a second side of said semi-permeable membrane being sufficiently less than the partial pressure of said unsaturated hydrocarbon in said vaporous mixture to provide separated unsaturated hydrocarbon on said second side of said semi-permeable membrane, and removing separated unsaturated hydrocarbon from the vicinity of said second side of said semi-permeable membrane, the improvement which comprises providing hydrogen peroxide in said aqueous liquid barrier in an amount sufficient to retard reduction of the ions in said ion component.

11. The method of claim 10 in which the separated unsaturated hydrocarbon is ethylene.

12. The method of claim 11 wherein said aqueous liquid barrier contains from about 0.1% to about 3% by weight of hydrogen peroxide based on the weight of the aqueous liquid barrier, and the concentration of the silver-containing ions in the aqueous liquid barrier is at least about 0.1 molar.

13. The method of claim 12 wherein said complex-forming silver-containing ion component includes silver nitrate.

14. The method of claim 11 wherein said semi-permeable membrane is hydrophilic.

15. The method of claim 14 wherein said membrane film comprises nylon.

16. The method of claim 15 wherein said membrane comprises nylon and polyvinyl alcohol.

* * * * *

UNITED STATES PATENT OFFICE
CERTIFICATE OF CORRECTION

PATENT NO. : 4,014,665
DATED : March 29, 1977
INVENTOR(S) : Edward F. Steigelmann It is certified that error appears in the above-identified patent and that said Letters Patent are hereby corrected as shown below:

Column 1, line 24, the word "for" should be --from--.

Column 1, line 52, the word "atoms" second occurrence, should be --atom--.

Column 1, line 61, the word "at", second occurrence should be -- or --.

Column 1, line 67, the word "mixtures" should be --mixture--.

Column 2, line 14, the word "impremeable" should be --impermeable--.

Column 3, line 53, after the word "solution", the following words were omitted --to form the film, said liquid solution--.

Column 5, line 12, the word "perferably" should be --preferably--.

Column 5, line 32, the word "of" should be --at--.

Column 5, line 59, the word "be" should be --by--.

Column 7, line 24, "5%" should be --50%--.

Column 7, line 28, "8" should be --18--.

Column 7, line 57, "155" should be --15%--.

Column 8, line 40, the word "adaquate" should be --adequate--.

UNITED STATES PATENT OFFICE
CERTIFICATE OF CORRECTION

PATENT NO. : 4,014,665
DATED : March 29, 1977
INVENTOR(S) : Edward F. Steigelmann It is certified that error appears in the above-identified patent and that said Letters Patent are hereby corrected as shown below:

Column 10, line 18, the word "the" first occurrence, should be --are--.

Column 10, line 54, after the word "inch" the word --inner-- was omitted.

Column 12, line 9, "EXAMPLE III-V" should read --EXAMPLES III-V--.

Column 12, line 26, the word "in" should be --was--.

Column 12, line 45, the word "obtaind" should be --obtained--.

Column 12, line 61, the word "with" should be --and--.

Column 13, line 37, in claim 3, the word "avbout" should be --about--.

Signed and Sealed this ninth Day of August 1977

[SEAL]

Attest:

RUTH C. MASON
Attesting Officer

C. MARSHALL DANN
Commissioner of Patents and Trademarks